United States Patent
Castro

(10) Patent No.: US 8,246,683 B2
(45) Date of Patent: *Aug. 21, 2012

(54) SPINAL IMPLANT

(75) Inventor: Frank Castro, Louisville, KY (US)

(73) Assignee: Cardinal Spine, LLC, Louisville, KY (US)

( * ) Notice: Subject to any disclaimer, the term of this patent is extended or adjusted under 35 U.S.C. 154(b) by 388 days.

This patent is subject to a terminal disclaimer.

(21) Appl. No.: 12/583,865

(22) Filed: Aug. 27, 2009

(65) Prior Publication Data

US 2010/0324682 A1 Dec. 23, 2010

Related U.S. Application Data

(63) Continuation-in-part of application No. 12/290,069, filed on Oct. 27, 2008, which is a continuation-in-part of application No. 12/221,779, filed on Aug. 6, 2008, now Pat. No. 8,002,832, which is a continuation of application No. 11/089,103, filed on Mar. 24, 2005, now Pat. No. 7,435,261.

(51) Int. Cl.
*A61F 2/44* (2006.01)

(52) U.S. Cl. .................................. 623/17.11; 623/17.16

(58) Field of Classification Search ..... 623/17.11–17.16
See application file for complete search history.

(56) References Cited

U.S. PATENT DOCUMENTS

| | | | |
|---|---|---|---|
| 4,892,545 A * | 1/1990 | Day et al. ................... | 623/17.11 |
| 5,147,402 A | 9/1992 | Bohler et al. | |
| 5,192,327 A | 3/1993 | Brantigan | |
| 5,405,391 A * | 4/1995 | Hednerson et al. ........ | 623/17.15 |
| 5,425,772 A | 6/1995 | Brantigan | |
| 5,522,899 A | 6/1996 | Michelson | |
| 5,558,674 A | 9/1996 | Heggeness et al. | |
| 5,609,635 A | 3/1997 | Michelson | |
| 5,766,252 A | 6/1998 | Henry et al. | |
| 6,066,175 A | 5/2000 | Henderson et al. | |
| 6,080,193 A | 6/2000 | Hochshuler et al. | |
| 6,090,143 A * | 7/2000 | Meriwether et al. ....... | 623/17.11 |
| 6,117,174 A | 9/2000 | Nolan | |
| 6,159,245 A | 12/2000 | Meriwether et al. | |
| 6,231,610 B1 | 5/2001 | Geisler | |
| 6,287,343 B1 | 9/2001 | Kuslich et al. | |
| 6,302,914 B1 * | 10/2001 | Michelson ................. | 623/17.16 |
| 6,395,030 B1 | 5/2002 | Songer et al. | |

(Continued)

FOREIGN PATENT DOCUMENTS

GB 2364643 2/2002

OTHER PUBLICATIONS

Barack, R. L. Revision Totatl Hip Arthroplasty: The Femoral Component. J. Am Acad Orthop Surg 1995; 3(2); 79-85. USA.

(Continued)

*Primary Examiner* — Eduardo C Robert
*Assistant Examiner* — Jerry Cumberledge
(74) *Attorney, Agent, or Firm* — Kenneth F. Pearce

(57) ABSTRACT

The present invention is a spinal implant that can be inserted into a surgically created cavity of one or more regions of the mammalian spine. Universal corner posts and one or more lateral universal posts are connected with a series of trapezoidal-like dividers. Embodiments of the cage can also include grips and superior and inferior plates.

18 Claims, 4 Drawing Sheets

U.S. PATENT DOCUMENTS

| | | | |
|---|---|---|---|
| 6,395,035 B2 | 5/2002 | Bresina et al. | |
| 6,409,766 B1 | 6/2002 | Brett | |
| 6,432,107 B1* | 8/2002 | Ferree | 606/247 |
| 6,491,724 B1 | 12/2002 | Ferree | |
| 6,537,320 B1 | 3/2003 | Michelson | |
| 6,569,201 B2 | 5/2003 | Moumene et al. | |
| 6,576,016 B1 | 6/2003 | Hochshuler et al. | |
| 6,641,614 B1 | 11/2003 | Wagner et al. | |
| 6,660,038 B2 | 12/2003 | Boyer, II et al. | |
| 6,712,825 B2 | 3/2004 | Aebi et al. | |
| 6,712,852 B1 | 3/2004 | Chung et al. | |
| 6,746,484 B1 | 6/2004 | Liu et al. | |
| 6,761,738 B1 | 7/2004 | Boyd | |
| 6,767,367 B1 | 7/2004 | Michelson | |
| 6,776,798 B2 | 8/2004 | Camino et al. | |
| 6,805,714 B2 | 10/2004 | Sutcliffe | |
| 6,808,538 B2 | 10/2004 | Paponneau | |
| 6,837,905 B1* | 1/2005 | Lieberman | 623/17.16 |
| 6,863,673 B2 | 3/2005 | Gerbec et al. | |
| 6,926,737 B2 | 8/2005 | Jackson et al. | |
| 6,942,697 B2 | 9/2005 | Lange et al. | |
| 6,997,953 B2 | 2/2006 | Chung et al. | |
| D524,942 S | 7/2006 | Felix | |
| 7,166,110 B2 | 1/2007 | Yundt | |
| 7,182,782 B2* | 2/2007 | Kirschman | 623/17.11 |
| 7,232,463 B2 | 6/2007 | Falahee | |
| 7,435,261 B1 | 10/2008 | Castro | |
| 7,618,460 B2* | 11/2009 | Boyd | 623/17.16 |
| 7,641,701 B2 | 1/2010 | Kirschman | |
| 7,942,932 B2 | 5/2011 | Castro | |
| 8,002,832 B2 | 8/2011 | Castro | |
| 2002/0128652 A1* | 9/2002 | Ferree | 606/61 |
| 2003/0125739 A1 | 7/2003 | Bagga et al. | |
| 2004/0064184 A1 | 4/2004 | Chung et al. | |
| 2004/0073314 A1 | 4/2004 | White et al. | |
| 2004/0126407 A1 | 7/2004 | Falahee | |
| 2004/0153155 A1 | 8/2004 | Chung et al. | |
| 2004/0153160 A1 | 8/2004 | Carrasco | |
| 2004/0199256 A1* | 10/2004 | Wang | 623/17.12 |
| 2004/0204714 A1 | 10/2004 | Liu et al. | |
| 2004/0225360 A1 | 11/2004 | Malone | |
| 2005/0071006 A1 | 3/2005 | Kirschman | |
| 2005/0071008 A1* | 3/2005 | Kirschman | 623/17.11 |
| 2005/0149192 A1* | 7/2005 | Zucherman et al. | 623/17.11 |
| 2005/0159813 A1 | 7/2005 | Molz, IV et al. | |
| 2006/0287725 A1 | 12/2006 | Miller | |
| 2007/0016295 A1 | 1/2007 | Boyd | |
| 2007/0129805 A1 | 6/2007 | Braddock | |
| 2007/0255409 A1 | 11/2007 | Dickson et al. | |
| 2007/0255413 A1 | 11/2007 | Edie et al. | |
| 2008/0015694 A1 | 1/2008 | Tribus | |
| 2008/0021476 A1 | 1/2008 | Kirschman | |
| 2008/0132901 A1 | 6/2008 | Recoules-Arche et al. | |
| 2008/0154377 A1 | 6/2008 | Voellmicke | |
| 2008/0275506 A1 | 11/2008 | Baynham | |
| 2009/0036985 A1 | 2/2009 | Whiting | |
| 2009/0234364 A1 | 9/2009 | Crook | |
| 2010/0004752 A1 | 1/2010 | White et al. | |

OTHER PUBLICATIONS

Castro, F. P., Jr. Stingers, Cervical Cord Neurapraxia, and Stenois. Clin Sport Med 2003; 22: 483-492. USA.

Majd M.E., Vadhva, M., Holt R.T. Anterior Cervical Reconstruction Using Titanium Cages With Anterior Plating. Spine 1999; 24 (15): 1604-1610. USA.

Park J.B., Cho Y.S., Riew, K.D. Development of Adjacent-Level Ossification in Patient with an Anterior Cervical Plate. J. Bone Surg. 1005; 87-A: 558-563. USA.

* cited by examiner

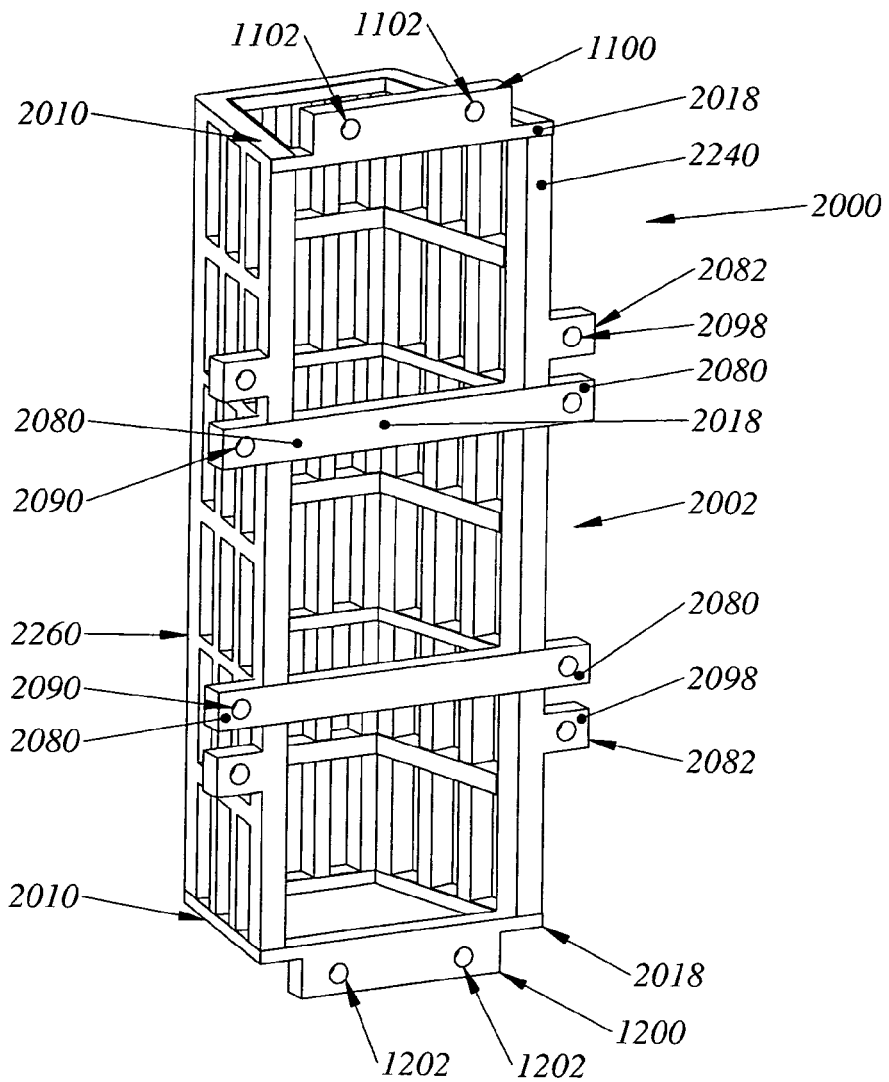
*FIG. 4*
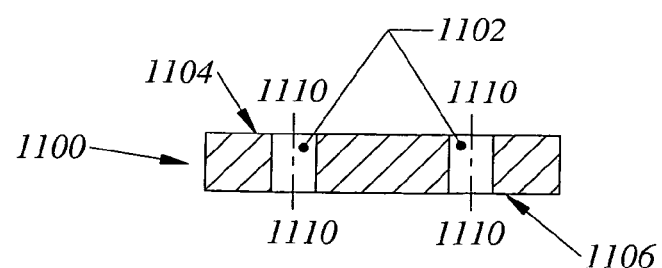
*FIG. 5*
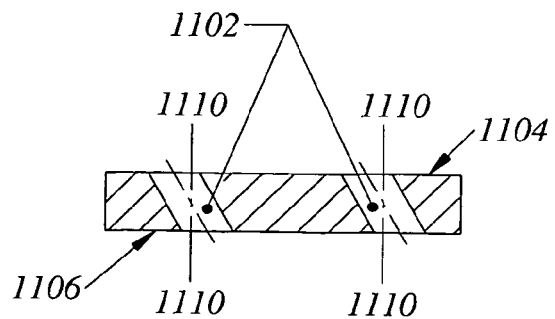

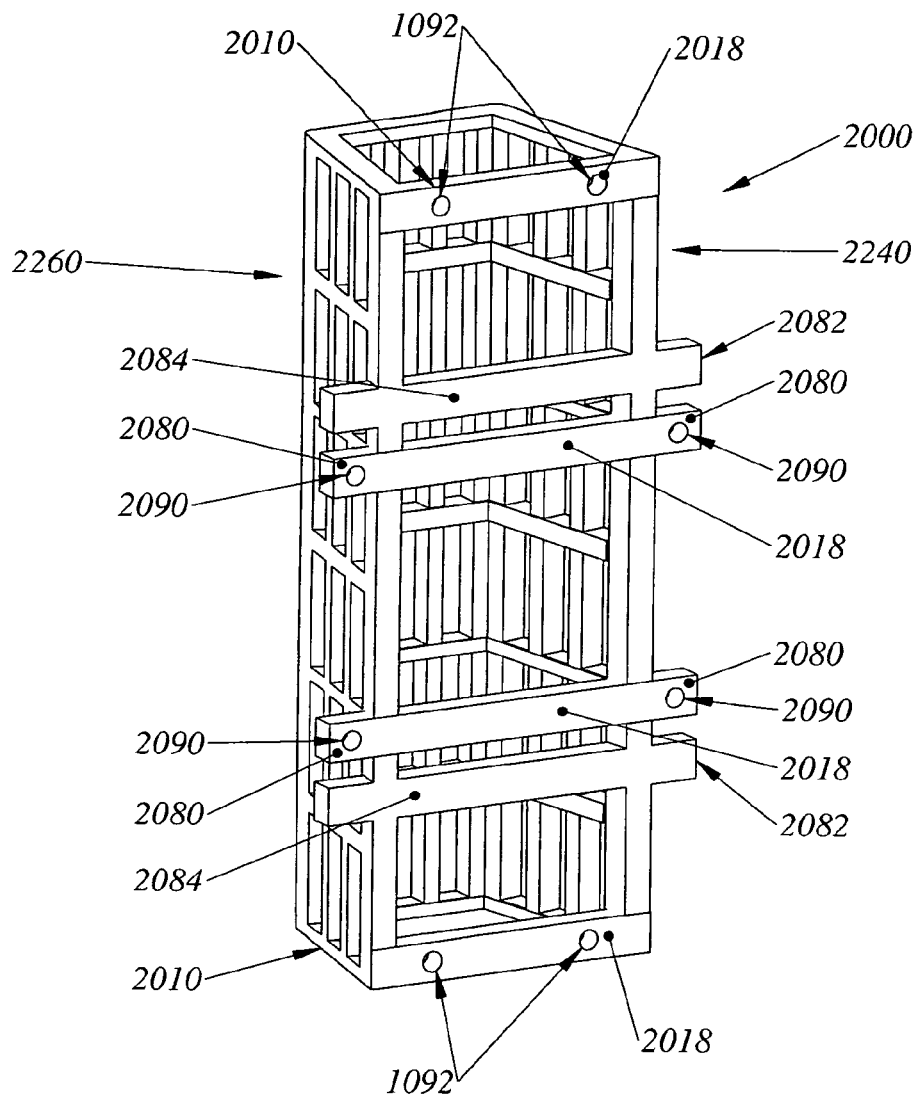
*FIG. 6*
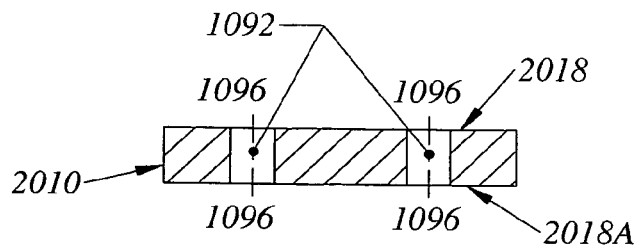
*FIG. 7*
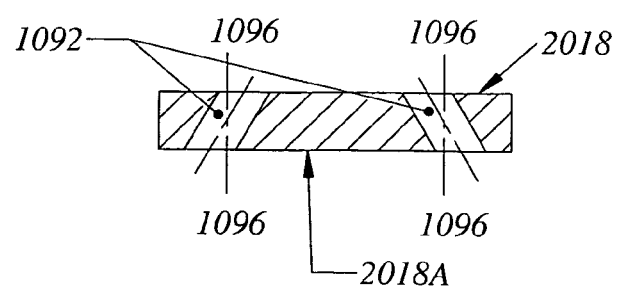

SPINAL IMPLANT

This application is a Continuation-in-Part of pending application for Letters patent Ser. No. 12/290,069 entitled—Spinal Implant and Method of Using Spinal Implant—filed on Oct. 27, 2008 that is a Continuation-in-Part of pending Application for Letters patent Ser. No. 12/221,779, entitled—Spinal Implant and Method of Using Spinal Implant—filed on Aug. 6, 2008 now U.S. Pat. No. 8,002,832 that is a Continuation of application for Letters patent Ser. No. 11/089,103, entitled—Spinal Implant and Method of Using Spinal Implant—filed on Mar. 24, 2005, now U.S. Pat. No. 7,435,261 B2 issued on Oct. 14, 2008.

BACKGROUND OF THE INVENTION

A. Field of the Invention

Among other things, the present invention is related to a surgical implant or cage that can be inserted into a cavity that has been created by removing spinal tissue. The cage includes a series of trapezoidal dividers or braces, first and second universal corner posts and lateral universal posts manufactured in such a way that the surgeon can see through the cage's openings prior to the addition of substances. In preferred embodiments, the spinal implant includes one or more laterally extending grips that can also function as brakes. One or more grip members can include bores for receiving fasteners. Other preferred embodiments of the current spinal implant are provided with superior and inferior plates having bores that can receive fasteners.

B. Description of the Previous Art

1) US Published Patent Application No. 20030125739 A1—Bagga, et al. discloses a bioactive spinal implant and method of manufacture. Among other things, it does not appear that the Bagga invention practices the use of a series of dividers, universal corner posts, universal posts or laterally extending grips.

2) U.S. Pat. No. 6,767,367 B1—Michelson enables a spinal fusion implant having deployable bone engaging projections. Michelson teaches that the '367 implant 300 has a rotatable member 320 that is preferably frustoconical in shape. Rotatable member 320 has bone engaging projections 332 adapted to penetrably engage the bone of the adjacent vertebral bodies. Bone engaging projections 332 are preferably configured such that in a retracted position, implant 300 may be linearly inserted into the disc space. After implant 300 is inserted into the disc space, bone engaging projections 332 are moved to a deployed position to penetrably engage the endplates of each adjacent vertebral body and prevent the expulsion of implant 300 from the disc space.

3) U.S. Pat. No. 6,537,320 B1—Michelson enables a self-broaching, rotable, push-in interbody spinal fusion implant and method for its deployment. Among other things, it does not appear that the Michelson invention practices the use of a series of dividers, universal corner posts, universal posts or grips.

4) U.S. Pat. No. 5,609,635—Michelson enables a lordotic interbody spinal fusion implant. The Michelson Summary of the Invention teaches, "In the preferred embodiment of the modular implant, the implant is again wedge-shaped in the side elevational view and is taller at its insertion end than at its trailing end." Being taller at an insertion end than at the trailing end is a teaching that is incompatible with the current spinal implant. Further, among other things, it does not appear that the Michelson invention practices the use of a series of dividers, universal corner posts, universal posts or grips.

5) U.S. Pat. No. 6,302,914 B1—Michelson enables a lordotic interbody spinal fusion implant. The '914 patent is a continuation Patent of the 5,609,635-Michelson Patent and enables the same limitations as the '635 patent.

6) U.S. Pat. No. 6,066,175—Henderson, et al. enables a fusion stabilization chamber. Henderson discloses a mesh cage 41, barrel vaults 48 and 49 and flanges 50 and 51 to anchor the cage. The cage is preferably rectangular when viewed from the top or the bottom. Among other things, it does not appear that the Henderson invention practices the use of a series of dividers, universal corner posts or universal posts.

7) U.S. Pat. No. 5,766,252—Henry, et al. enables an interbody spinal prosthetic implant and method. Henry requires a threaded hole 38 to practice the '252 invention. Among other things, it does not appear that the Henry invention practices the use of a series of dividers, universal corner posts, universal posts or grips.

8) U.S. Pat. No. 5,425,772—Brantigan enables a prosthetic implant for intervertibral spinal fusion. The '772 device practices traverse teeth or serrations 19 where the teeth have sharp peaks 19a, slopping walls 19b and valleys 19c. Among other things, it does not appear that the Brantigan invention practices the use of a series of dividers, universal corner posts, universal posts or grips.

9) U.S. Pat. No. 5,147,402—Bohler, et al. enables an implant for ingrowth of osseous tissue. Among other things, it does not appear that the Bohler invention practices the use of a series of dividers, universal corner posts, universal posts or grips.

10) U.S. Pat. No. 6,746,484—Liu, et al. enables a spinal implant. Among other things, Liu teaches an implant 1 having an elongate hollow body 3, parallel longitudinal walls 4 and terminal ends 5 and 6 including threaded holes 11a. Among other things, it does not appear that the Liu invention practices the use of a series of dividers, universal corner posts, universal posts or grips.

11) U.S. Pat. No. 6,231,610 B1—Geisler enables an anterior cervical column support device. The '610 apparatus utilizes serrations on the load bearing surfaces and two screw holes. Among other things, it does not appear that the Geisler invention practices the use of a series of dividers, universal corner posts, universal posts or grips.

12) U.S. Pat. No. 6,660,038 B2—Boyer, et al. enables skeletal reconstruction cages. The Boyer Patent discloses an end cap 210 suitable for coupling to central shaft 160 includes an outer wall 212, as well as a central hole disposed along axis 213 with a lower inner wall 214, an upper inner wall 216, and an inner ridge portion 218. Notably, while outer wall 176 of central shaft 160 is generally circular, outer wall 212 of end cap 210 is generally oblong, so that a generally I-shaped skeletal reconstruction cage may be formed when a pair of end caps 210 are placed on central shaft 160. Among other things, it does not appear that the Boyer invention practices the use of a series of dividers, universal corner posts, universal posts or grips.

13) U.S. Pat. No. 6,491,724—Ferree enables a spinal fusion cage with lordosis correction. Among other things, Ferree teaches an anterior portion 112 that includes mating members 120 and 122 with teeth 124 or other features to form a locking or ratchet mechanism that is used to alter the height of the cage. Among other things, it does not appear that the Ferree invention practices the use of a series of dividers, universal corner posts, universal posts or grips.

14) U.S. Pat. No. 6,117,174—Nolan enables a spinal implant device that has disc 14 made of the same material as body 12. Among other things, it does not appear that the Nolan invention practices the use of a series of dividers, universal corner posts, universal posts or grips.

15) US Published Patent Application No. 20070016295—Boyd discloses a reinforced molded implant formed of cortical bone. Boyd reads, "Implant 10 defines a longitudinal axis 11 and includes a first strut 12, a second strut 14 spaced from first strut 12, and cross-member 16 extending therebetween. First strut 12 and second strut 14 are each positioned to lie in a plane substantially parallel to longitudinal axis 11. Implant 10 includes at least one additional cross-member 16 A connecting first strut 12 and second strut 14. It is understood that in alternative embodiments implant 10 can have one or a plurality of cross-members connecting first strut 12 to second strut 14."

16) U.S. Pat. No. 6,090,143—Meriwether, et al. enables a box cage for intervertebral body fusion. Meriwether reads, "FIG. 6 illustrates a further embodiment of the invention which is a slight modification of that shown in FIG. 4. In the embodiment of FIG. 6, rather than having a rectangular longitudinal cross-section, it is trapezoidal such that the resulting cage member, indicated generally by numeral 110, is wedge-shaped. The assembled cage comprises a box-like base 112 and a cover 114 dimensioned to fit over the base much like the cover on a shirt box. The height dimension of the rightmost ends of the base and cover are greater than the height dimension of the corresponding, opposed left side ends, thus providing the desired wedge shape. Upwardly projecting ribs 116 and 118 extend along the rear and front side edges, respectfully, and likewise, the base 112 includes longitudinally extending ribs 120 and 122 projecting downwardly from the undersurface of the base along the side edges thereof. The right and left ends of the base 112 and the cover 114 include semi-circular cut-outs as at 124 and 126 and 128-130 such that when the cover 114 is placed upon the base 112, circular apertures are formed. These apertures are adapted to receive a tapered screw 132 therein. The slope of the taper of the screw is designed to correspond to that of the cage assembly 110 such that when the screw 132 is threaded into the circular opening defined by arcuate cut-outs 124 and 126 and advanced by turning until the leading end 134 of the screw enters the circular aperture 128-130, further turning of the screw will raise the case cover 114 relative to its base 112, allowing adjustment of the cage height following positioning thereof between adjacent vertebral bodies."

17) U.S. Pat. No. 6,159,245—Meriwether, et al. enables a box cage for intervertebral body fusion. The '245 Meriwether Patent is a continuation of U.S. Pat. No. 6,090,143—Meriwether, et al. and teaches the same limitations as the '143 patent.

18) U.S. Pat. No. 6,432,107—Ferree enables enhanced surface area spinal fusion devices. The '107 patent teaches, "The device 200 fits into slots 204 and 206 made in upper and lower vertebrae 208 and 210, respectively, allowing the lower section to fuse within the body of the lower vertebrae 210, and the upper section to fuse within the body of the upper vertebrae 208. Thus, in contrast to existing devices, the device 200 and the alternative embodiments disclosed herein feature considerably more intimate contact with cancellous bone due to the fact that the device is inserted directly into the cavities 204 and 206. Rather than a relatively minor amount of scraping of the end plates of the vertebrae to be distracted, the entire end portions of the device 200 which penetrate the upper and lower vertebrae make contact with cancellous bone, thereby enhancing fusion considerably. FIG. 2B is a cross-section of a vertebrae of FIG. 2A as viewed from a top-down perspective, showing how the device fits tightly along the entire walls of the channels created in the vertebrae." Among other things, the Ferree device does provide a series of dividers, receptacles visible to the surgeon after insertion into the surgical cavity or grips.

19) U.S. Pat. No. 6,569,201—Moumene, et al. enables a hybrid composite interbody fusion device. Moumene's Osteoconductive pore 2 forms a void 23 within the support and defines an inner surface 13, and opens onto side surface openings 19, 21 formed in side surfaces 7, 9, and the void section 23 is suitable for housing a bone growth material such as bone chips (not shown). Among other things, it does not appear that the Moumene invention practices the use of a series of dividers, universal corner posts, universal posts or grips.

SUMMARY OF THE INVENTION

Unlike traditional spinal implants, the present invention provides a spinal implant that can be packed with bone graft and/or other osteogenic materials or substances after the spinal implant has been inserted into a cavity created by the removal of spinal tissue. After the implant is inserted into the surgically created cavity and prior to insertion of osteogenic substances, the surgeon can view the dura mater of the spinal cord. During surgical procedures, the trapezoidal-like cage assists the surgical team in not impinging the spinal cord with the implant. Post operative and prior to complete arthrodesis, the implant also inhibits extrusion of the cage against the spinal cord.

An aspect of the present invention is to provide a cage having a series of trapezoidal dividers or braces, first and second universal corner posts and lateral universal posts.

Another aspect of the present invention is to provide an implant having select embodiments that can be implanted through the patient's frontal or rearward side.

Yet still another aspect of the present invention is to provide a cage that can be severed across a first cross-section or severed across a first cross-section and a second cross-section to create a custom fitted implant for the surgically created cavity.

Still another aspect of the present invention is to provide a cage including one or more laterally extending grips that can also function as brakes.

It is still another aspect of the present invention to provide an implant having a plurality of apertures the surgeon can see through prior to addition of osteogenic and/or arthrodesis accelerating substances or other substances.

Another aspect of the present invention is to provide an implant that includes grips with one or more member having bores for receiving fasteners such as bone screws.

Yet another aspect of the present invention is to provide an implant that includes upper and lower plates having one or more bores for receiving fasteners.

An embodiment of the present invention can be described as a spinal implant consisting essentially of titanium, stainless steel, resorbable polymers, non-resorbable polymers or combinations thereof where the spinal implant comprises a length of consecutively joined receptacles having peripheral openings a surgeon can see through prior to addition of osteogenic and/or arthrodesis accelerating substances, wherein the length of consecutively joined receptacles comprises: a) a series of trapezoidal dividers having a common lengthwise axis, wherein each divider comprises: i) an inward side; ii) an outward side; iii) a first side connected with the outward side and the inward side forming a first outward corner with the outward side and a first inward corner with the inward side; iv) a second side connected with the outward side and the inward side forming a second outward corner with the outward side and a second inward corner with the inward side; and v) an aperture; b) a first universal corner post contacting the first inward corners; c) a second universal corner post contacting the second inward corners; d) one or more first universal posts contacting the first sides of the dividers; e) one or more second universal posts contacting the second sides of the dividers; f) one or more inward universal posts contacting the inward sides of the dividers; g) one or more bars, parallel to one or more of the outward sides of the series, contacting one of the first universal posts and one of the second universal posts; h) one or more first side brakes, comprising a bore, proximate to one or more first outward corners and extending laterally beyond the first sides; and i) one or more second side brakes, comprising a bore, proximate to one or more second outward corners and extending laterally beyond the second sides.

Another embodiment of the present invention can be described as a cage including peripheral openings a surgeon can see through prior to addition of osteogenic and/or arthrodesis accelerating substances and capable of implantation into a cavity surgically created between a superior spinal region and an inferior spinal region of a mammal; the cage comprising: a) a series of trapezoidal dividers; b) a first universal corner post contacting first inward corners of the series; c) a second universal corner post contacting second inward corners of the series; d) one or more first universal posts contacting first lateral sides of the series; e) one or more second universal posts contacting second lateral sides of the series; f) one or more inward universal posts contacting inward lateral sides of the series; and g) a grip comprising: i) one or more first pairs of lateral extensions contacting an outward first universal post and extending laterally beyond first lateral sides of the series; and ii) one or more second pairs of lateral extensions contacting an outward second universal post and extending laterally beyond second lateral sides of the series.

Another embodiment of the present invention can be described as a cage capable of implantation into a cavity surgically created between a superior spinal region and an inferior spinal region of a mammal; the cage comprising: a) a series of trapezoidal braces; b) an inward support; c) an outward support; d) a first lateral support; e) a second lateral support; and f) a grip comprising: i) one or more first pairs of lateral extensions contacting the outward support and extending laterally beyond the first lateral support; and ii) one or more second pairs of lateral extensions contacting the outward support and extending laterally beyond the second lateral support.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 4 is a frontal perspective of another embodiment of the present invention.

FIG. 5 is a cross section of an embodiment of a plate of the present invention.

FIG. 6 is a frontal perspective of yet another embodiment of the present invention.

FIG. 7 is a cross section of an embodiment of an outward side and inward edge of a superior or inferior brace of the present invention.

DESCRIPTION OF THE PREFERRED EMBODIMENTS

Figure 1:
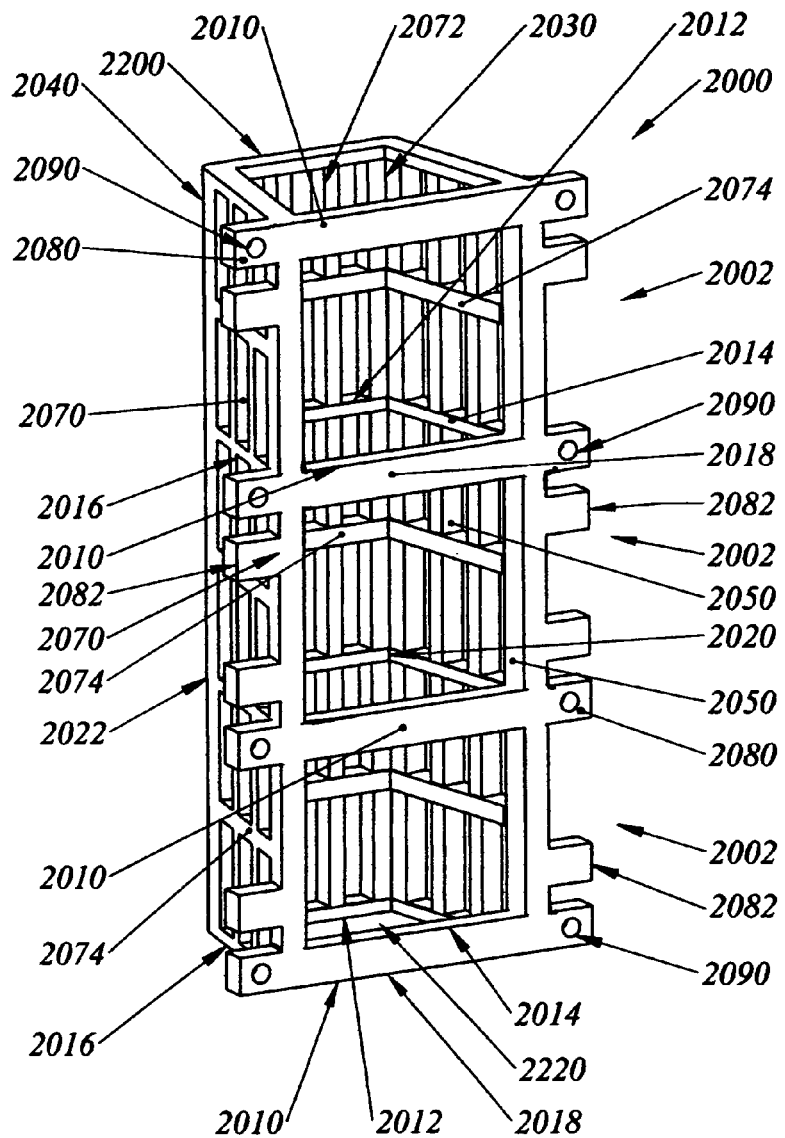
FIG. 1 is a frontal perspective of an embodiment of the present invention.

Although the disclosure hereof is detailed to enable those skilled in the art to practice the invention, the embodiments published herein merely exemplify the present invention.

In the most general sense, the present invention is a cage or implant that can be inserted into a cavity of the spinal column. Surgical removal of mammalian spinal tissue in one or more spinal regions creates the cavity or cavities that will receive the implant or implants. It has been discovered that many embodiments of the current implant can be useful for cervical spine surgeries and can assist in stabilization of the postoperative spine. And many of the preferred embodiments of the present invention are particularly suited for corpectomy or partial corpectomy procedures.

After insertion of the implant into the cavity, the cage assists in stabilizing the spinal column against rotational movement and also resists the compression forces associated with gravity on the spinal column. Select preferred embodiments of the present invention can be implanted through the patient's anterior side, e.g., the frontal side of the patient's neck. The current spinal implants are custom fitted for the surgical cavity into which they will be inserted, i.e., the cage can be manufactured to fit the surgical cavity or the cage can be severed across a first cross section or the cage can be severed across first and second cross sections to size the cage to fit the cavity.

Preferred embodiments of the current spinal implant are generally trapezoidal in shape and are manufactured of titanium alloys, stainless steel, resorbable polymers, non-resorbable polymers or any other composition acceptable in the art. Within the scope of the present invention, it has advantageously been discovered that the cage can have a width of from about six to about fifteen millimeters, as measured along the narrowest parallel of the trapezoid, and a depth of from about eight millimeters to about fifteen millimeters, as measured along a converging side of the trapezoid. Generally the spacing between dividers of the cage is approximately twelve millimeters, as measured from outward side to outward side of the series of dividers. Openings of the sides of the cages of the current invention into which bone graft, osteogenic and/or arthrodesis accelerating substances are packed can have areas from about 36 millimeters$^2$ to 225 millimeters$^2$ or greater.

Universal corner posts and lateral universal posts are spaced about the outer border of the cage. Select preferred embodiments include one or more grips. Among other things, the grips can function as brakes. One or more the grip members can be provided with a bore for receiving a fastener, such as a screw. In other preferred embodiments, one or more ties can extend about the implant and contact the universal posts and the universal corner posts. Universal corner posts and universal posts are from about one millimeter to about two millimeters wide and are situated along the outer periphery of the cage in such a way as to create apertures between the universal lateral posts and the universal corner posts. Depending on the volume of the implant, spacing between the universal corner posts and the lateral universal posts and between the lateral universal posts is from about one millimeter to about two millimeters.

Meeting a long felt but unfilled need in the spinal surgical arts, the unique structures of the present invention allow the surgical team to view the dura mater, before the cage is packed with bone graft, osteogenic and/or arthrodesis accelerating substances. Allowing the surgical team to view the dura mater while inserting the implant into the cavity reduces the possibility of having the cage inadvertently contact or injure the spinal cord. Contact between the surgical cavity wall and the cage and/or its grip/brake members can also inhibit the implant from contacting the spinal cord. It appears that having the apertures of select embodiments in such close proximity with the cavity's walls increases the probability of the osteogenic materials procuring a blood supply. And it is believed that increasing the blood supply to the osteogenic materials held by the cage enhances local areas of arthrodesis between the vertebra and the bone graft.

Among other things, FIG. 1 enables a cage (2000) having a series of trapezoidal dividers (2010) and a plurality of receptacles (2002) that can be packed with osteogenic materials or other substances prior to the completion of spinal surgery. Cage (2000) is manufactured of titanium, stainless steel, resorbable polymers, non-resorbable polymers or combinations thereof. By way of illustration, generally horizontal dividers or braces (2010) have inward sides (2012) (after insertion into the surgically created cavity, positioned near the dura mater of the spinal cord), outward sides (2018) (proximate the surgeon after insertion into the surgically created cavity), first converging or lateral sides (2014) and second converging or lateral sides (2016). Intersection of first lateral sides (2014) and inward sides (2012) create first corners (2020) and intersection of inward sides (2012) and second lateral sides (2016) creates second corners (2022), such that each brace (2010) has first corner (2020) and second corner (2022).

First universal corner post (2030) contacts first corners (2020) and second universal corner post (2040) contacts second corners (2022). In the embodiment disclosed in FIG. 1, first universal corner post (2030) is angled at about ninety degrees to simultaneously connect with inward sides (2012) and first lateral sides (2014) of generally horizontal dividers (2010) and second universal corner post (2040) is angled at about ninety degrees to simultaneously connect with inward sides (2012) and second lateral sides (2016) of braces (2010). In other preferred embodiments, universal corner posts (2030 and 2040) are not angled at about ninety degrees.

In select embodiments, one or more first side universal posts (2050) contact first lateral sides (2014) of cage (2000), one or more second side universal posts (2070) contact second lateral sides (2016) of cage (2000) and one or more inward universal posts (2072) contact inward sides (2012) of cage (2000). One of the first side universal posts (2050) is generally proximate outward sides (2018) of brace (2010), and in a similar vein, one of the second side universal posts (2070) is generally proximate outward sides (2018) of braces (2010).

Inward support (2200) of cage (2000) includes inward sides (2012) of braces (2010) and universal corner posts (2030 and 2040). First lateral support (2240) of cage (2000) includes lateral sides (2014) of braces (2010), universal corner post (2030) and one or more universal posts (2050). Second lateral support (2260) of cage (2000) includes lateral sides (2016) of braces (2010), universal corner post (2040) and one or more universal posts (2070). Outward support (2220) of cage (2000) includes outward sides (2018) of braces (2010), an outward universal post (2050) and an outward universal post (2070).

Select preferred embodiments of cage (2000) can also include inward universal posts (2072) contacting generally inward sides (2012) of generally horizontal dividers (2010). Still other preferred embodiments of cage (2000) can include one or more ties (2074) contacting universal corner posts (2030, 2040) and universal posts (2050, 2070 and 2072). Most preferably, ties (2074) are positioned on the inward sides of the universal posts (2030, 2040, 2050, 2070 and 2072).

The combination of braces (2010), universal corner posts (2030 and 2040), universal posts (2050, 2070 and 2072) and ties (2074) creates openings of more than one cross-sectional area about the outer border of cage (2000)—allowing the surgeon to see through the openings, prior to the addition of osteogenic or other substances into implant (2000).

In the preferred embodiment exemplified in FIG. 1, cage (2000) is provided with a plurality of lateral extensions or brakes (2080 and 2082). As shown brakes (2080) are integral with one or more outward sides (2018) of dividers (2010). However, in other preferred embodiments of current invention, lateral extensions (2080) need not be integral with outward sides (2018) of braces (2010). In other words, lateral extensions (2080 and 2082) can be affixed with outward universal posts (2050 and/or 2070) in any manner acceptable in the art. The combination of lateral extensions (2080 and 2082) can function as a grip for cage (2000). It has been discovered that the use of the grip improves a surgical instrument's gripping of implant (2000).

As shown in FIG. 1, one or more brakes (2080 and 2082) are provided with bore (2090). In the practice of the present invention, one or more lateral extensions (2080 and 2082) extend laterally beyond first lateral support (2240) or one or more lateral extensions (2080 and 2082) extend laterally beyond second lateral support (2260) or one or more lateral extensions (2080 and 2082) extend laterally beyond first lateral support (2240) and second lateral support (2260). Along with providing a grip, lateral extensions (2080 and 2082) assist the surgeon in minimizing potential damage to the spinal cord from over-insertion of the implant into the surgically created cavity.

Figure 2:
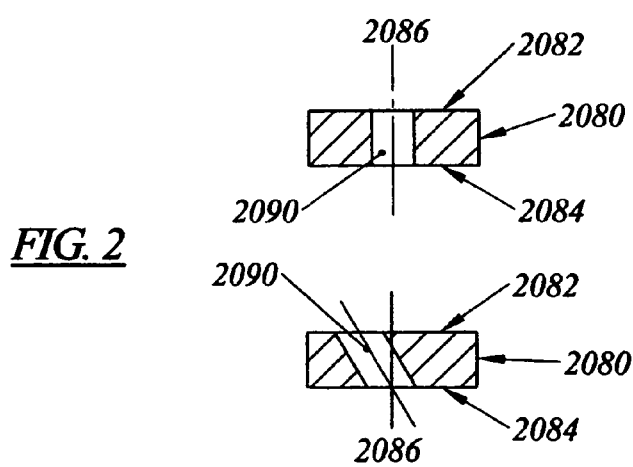
FIG. 2 is a cross section of an embodiment of a brake of the present invention.

Depending on predetermined engineering parameters, as shown in FIG. 2, lateral extension (2080) can include bore (2090) that is perpendicular to outward side (2082) and inward side (2084) of brake (2080) or lateral extension (2080) can include bore (2090) that is angled at other than perpendicular from the outward side (2082) and inward side (2084) of brake (2080). It has been discovered that bore (2090) can be angled from about 1 degree to about 60 degrees away from the bore's reference axis (2086-2086), where the reference axis (2086-2086) equates to the perpendicular axis between outward side (2082) and inward side (2084) of lateral extension (2080). Although not shown in FIG. 1 or 2, lateral extension (2082) can be provided with a bore having identical structures to those enabled for bore (2090).

In select preferred embodiments, bores (2090) of brakes (2080) associated with superior dividers (2010) can be angled upward from outward sides (2082) through inward sides (2084) of brakes (2080) and bores (2090) of brakes (2080) associated with inferior dividers (2010) can be angled downward from outward sides (2082) through inward sides (2084) of brakes (2080). Bores (2090) function to receive a fastener, such as a screw (not shown in this view), that assists in securing the implant to bone.

Figure 3:
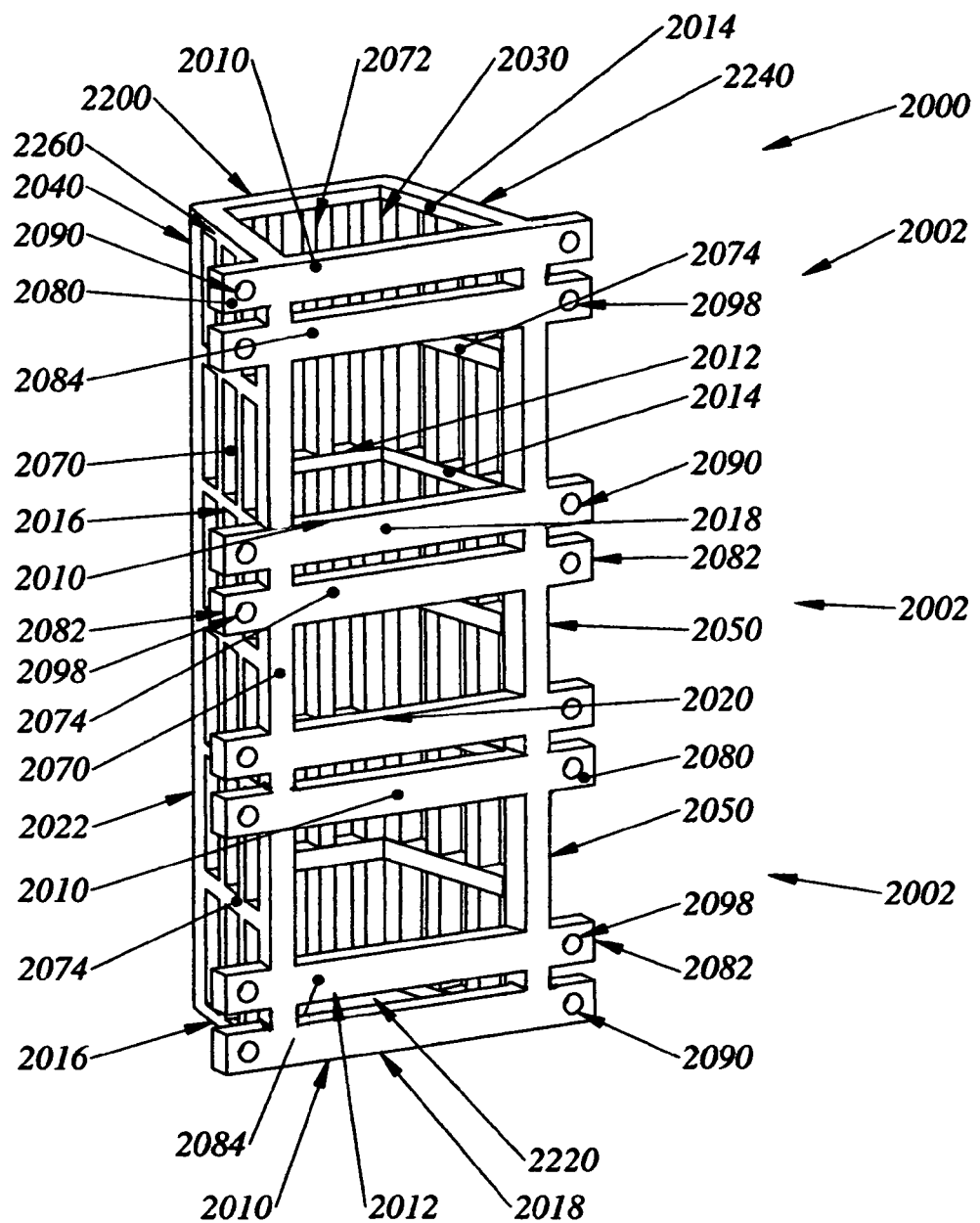
FIG. 3 is a frontal perspective of another embodiment of the present invention.

The preferred embodiment disclosed in FIG. 3 is similar to the preferred embodiment disclosed in FIG. 1. By way of illustration, one or more bars (2084) extending between lateral extensions (2082) and bores (2098) are not shown in FIG.

1. As shown in the FIG. 3 embodiment, bars (2084) are integral with lateral extensions (2082). In other embodiments, bars (2084) are not integral with lateral extensions (2082). As previously indicated, bores (2098) can be provided structures identical to those enabled for bore (2090).

As portrayed in FIG. 3 bars (2084) are proximate to and parallel with outward sides (2018) of braces (2010). Bars (2084) contact first side universal posts (2050) proximate outward sides (2018) of brace (2010) and second side universal posts (2070) proximate outward sides (2018) of brace (2010). Among other things, it has been discovered that the combination of outward sides (2018) and bars (2084) enhances the cage's resistance to bending, twisting or torsion. Further, testing reveals that the cage's structure is capable of withstanding greater compressive loads than round or oval implants.

Turning to the preferred embodiment disclosed in FIG. 4, implant (2000) is provided with a superior plate (1100) attached to outward side (2018) of superior brace (2010). In similar fashion, inferior plate (1200) is attached to outward side (2018) of inferior brace (2010). Upper plate (1100) has two bores (1102) for receiving fasteners, such as screws, to assist in securing cage (2000) to bone. Lower plate (1200) includes two bores (1202) for receiving fasteners that assist in securing cage (2000) to bone. Although upper plate (1100) and lower plate (1200) are shown with a plurality of bores, Applicant's current invention can function when upper plate (1100) and lower plate (1200) each include only a single bore (1102, 1202).

As shown in the embodiment of FIG. 4, superior plate (1100) extends upward from superior brace or divider (2010) and inferior plate (1200) depends downward from inferior brace or divider (2010). In select embodiments, superior plate (1100) extends upward in a plane perpendicular to outward side (2018) of superior brace (2010) and inferior plate (1200) depends downward in a plane perpendicular to outward side (2018) of inferior divider (2010). Proximate intermediate braces (2010) are one or more lateral extensions (2080 and 2082) that can be provided with bores (2090 and 2098). As shown, lateral extensions (2080 and 2082) extend laterally beyond first lateral support (2240) and second lateral support (2260) of implant (2000).

With reference to FIG. 5, plate (1100) can include one or more bores (1102) where each bore (1102) is perpendicular to outward side (1104) and inward side (1106) of plate (1100) or plate (1100) can include one or more bores (1102) that are angled at other than perpendicular from the outward side (1104) and inward side (1106) of plate (1100). By way of example, bores (1102) can be angled from about 1 degree to about 60 degrees away from the bore's reference axis (1110-1110), where the reference axis (1110-1110) equates to the perpendicular axis between outward side (1104) and inward side (1106) of plate (1000). Plate (1200) and one or more bores (1202) are manufactured in a similar fashion to plate (1100) and one or more bores (1102).

In select preferred embodiments, bores (1102) of plate (1100) are angled upward from outward side (1104) through inward side (1106) of plate (1100) and bores (1202) of plate (1200) are angled downward from the outward side of plate (1200) through the inward side of plate (1200) One or more bores (1102, 1202) function to receive a fastener, such as a screw (not shown in this view) that assists in securing the implant to bone. Select preferred embodiments can include lateral extensions (2080) that are not integral with outward sides (2018) of braces (2010).

With reference to the preferred embodiment portrayed in FIG. 6, implant (2000) is provided with superior brace (2010) that includes a plurality of bores (1092) integral with outward side (2018) and inward edge (2018A) of superior brace (2010). Inferior brace (2010) includes a plurality of bores (1092) integral with outward side (2018) and inward edge (2018A) of inferior divider (2010). Bores (1092) are inset from first lateral support (2240) and second lateral support (2260) of cage (2000). As depicted in FIG. 7, superior brace (2010) includes one or more bores (1092) where each bore (1092) is angled at other than perpendicular from the outward side (2018) and inward edge (2018A) of brace (2010). Bores (1092) can be angled from about 1 degree to about 60 degrees away from the bore's reference axis (1096-1096), where the reference axis (1096-1096) equates to the perpendicular axis between outward side (2018) and inward edge (2018A) of brace (2010). Inferior brace (2010) and one or more bores (1092) are manufactured in a similar fashion to superior brace (2010) and one or more bores (1092). In the preferred embodiments, bores (1092) of superior brace (2010) are angled upward from outward side (2018) through inward edge (2018A) of superior brace (2010) and bores (1092) of inferior brace (2010) are angled downward from the outward side (2018) through inward edge (2018A) of inferior brace (2010). Bores (1092) function to receive a fastener, such as a screw (not shown in this view) that assists in securing the implant to bone.

Having disclosed the invention as required by Title 35 of the United States Code, Applicant now prays respectfully that Letters Patent be granted for his invention in accordance with the scope of the claims appended hereto.

What is claimed is:

1. A spinal implant consisting essentially of titanium, stainless steel, resorbable polymers, non-resorbable polymers or combinations thereof; said spinal implant comprising a length of consecutively joined receptacles having peripheral openings a surgeon can see through prior to addition of osteogenic and/or arthrodesis accelerating substances, wherein said length of consecutively joined receptacles comprises:
  a) a series of trapezoidal dividers having a common lengthwise axis, wherein each divider comprises:
    i) an inward side;
    ii) an outward side;
    iii) a first side connected with said outward side and said inward side forming a first outward corner with said outward side and a first inward corner with said inward side;
    iv) a second side connected with said outward side and said inward side forming a second outward corner with said outward side and a second inward corner with said inward side; and
    v) an aperture;
  b) a first universal corner post contacting said first inward corners;
  c) a second universal corner post contacting said second inward corners;
  d) one or more first universal posts contacting said first sides of said dividers;
  e) one or more second universal posts contacting said second sides of said dividers;
  f) one or more inward universal posts contacting said inward sides of said dividers;
  g) one or more bars, parallel to one or more of said outward sides of said series, contacting one of said first universal posts and one of said second universal posts;
  h) one or more first side brakes, comprising a bore, proximate to said one or more first outward corners and extending laterally beyond said first sides; and i) one or more second side brakes, comprising a bore, proximate to said one or more second outward corners and extending laterally beyond said second sides.

2. The spinal implant of claim 1, wherein each said bar comprises:
   a) a first extension extending beyond said first sides; and
   b) a second extension extending beyond said second sides.

3. The spinal implant of claim 2 further comprising a plurality of ties contacting said first corner post, said second corner post, said first universal posts, said second universal posts and said inward universal posts.

4. The spinal implant of claim 3 wherein said first universal corner post is angled at about ninety degrees to simultaneously connect with said first inward corners of said series and said second universal corner post is angled at about ninety degrees to simultaneously connect with said second inward corners of said series.

5. The spinal implant of claim 4 wherein:
   a) an outward side of an outer divider of said series of trapezoidal dividers further comprises a plate including one or more bores therein; or
   b) an outward side of a first outer divider of said series of trapezoidal dividers further comprises a first plate including one or more bores therein and an outward side of a second outer divider of said series of trapezoidal dividers further comprises a second plate including one or more bores therein.

6. A cage including peripheral openings a surgeon can see through prior to addition of osteogenic and/or arthrodesis accelerating substances and capable of implantation into a cavity surgically created between a superior spinal region and an inferior spinal region of a mammal; said cage comprising:
   a) a series of trapezoidal dividers, wherein each said divider comprises an inward side, an outward side and opposing first and second lateral sides such that a combination of said sides creates an aperture;
   b) a first universal corner post contacting first inward corners of said series;
   c) a second universal corner post contacting second inward corners of said series;
   d) one or more first universal posts contacting first lateral sides of said series;
   e) one or more second universal posts contacting second lateral sides of said series;
   f) one or more inward universal posts contacting inward lateral sides of said series; and
   g) a grip comprising:
      i) one or more first pairs of lateral extensions contacting an outward first universal post and extending laterally beyond first lateral sides of said series, wherein each member of said pair of lateral extensions is generally parallel the other member and one of the members includes a bore; and
      ii) one or more second pairs of lateral extensions contacting an outward second universal post and extending laterally beyond second lateral sides of said series, where each member of said pair of lateral extensions is generally parallel the other member and one of the members includes a bore.

7. The cage of claim 6 further comprising a plurality of ties contacting said first corner post, said second corner post, said first universal posts and said second universal posts.

8. The cage of claim 7, wherein:
   a) a first one of said members of said first pairs of lateral extensions is an integral extension of said outward side of one or more of said trapezoidal dividers; and
   b) a first one of said members of said second pairs of lateral extensions is an integral extension of said outward side of one or more of said trapezoidal dividers.

9. The cage of claim 8 further comprising a bar integrally connecting with second members of said first pairs of lateral extensions and said second members of said second pairs of lateral extensions.

10. The cage of claim 9 wherein said first universal corner post is angled at about ninety degrees to simultaneously connect with said first inward corners of said series and said second universal corner post is angled at about ninety degrees to simultaneously connect with said second inward corners of said series.

11. A cage capable of implantation into a cavity surgically created between a superior spinal region and an inferior spinal region of a mammal; said cage comprising:
   a) a series of trapezoidal braces, wherein each trapezoidal brace includes two sides of equal length and an aperture;
   b) an inward support;
   c) an outward support;
   d) a first lateral support;
   e) a second lateral support, wherein said supports are joined with each other such that said outward support is of greater dimensions than said inward support and are generally transverse to a lengthwise axis of said cage; and
   f) a grip comprising:
      i) one or more first pairs of lateral extensions contacting said outward support and extending laterally beyond said first lateral support; and
      ii) one or more second pairs of lateral extensions contacting said outward support and extending laterally beyond said second lateral support.

12. The cage of claim 11, wherein:
   a) said inward support comprises:
      i) a first corner common with said first lateral support; and
      ii) a second corner common with said second lateral support; and
   b) said outward support comprises a border common with said first lateral support and said second lateral support.

13. The cage of claim 12, wherein each member of said pairs of lateral extensions is generally parallel the other member.

14. The cage of claim 13, wherein:
   a) a first one of said members of said first pairs of lateral extensions extends from an outward side of one or more of said trapezoidal braces; and
   b) a first one of said members of said second pairs of lateral extensions extends from said outward side of one or more of said trapezoidal braces.

15. The cage of claim 14, wherein at least two members of said pairs of lateral extensions further comprise bores.

16. The cage of claim 15 further comprising one or more bars connecting with second members of said first pairs of lateral extensions and said second members of said second pairs of lateral extensions.

17. The cage of claim 16, wherein said inward support and said lateral supports further comprise one or more posts and one or more ties.

18. The cage of claim 17, wherein said cage comprises: titanium, stainless steel, resorbable polymers, non-resorbable polymers or combinations thereof.

\* \* \* \* \*